United States Patent
Bartonek et al.

(10) Patent No.: US 9,518,947 B2
(45) Date of Patent: Dec. 13, 2016

(54) SYSTEM AND METHOD FOR DETECTING WHEEL BEARING CONDITION

(71) Applicant: Progress Rail Services Corporation, Albertville, AL (US)

(72) Inventors: Mark J. Bartonek, Independence, MO (US); Donald J. Arndt, Napoleon, MO (US); Roland F. O'Connell, Lone Jack, MD (US)

(73) Assignee: Progress Rail Services Corporation, Albertville, AL (US)

( * ) Notice: Subject to any disclaimer, the term of this patent is extended or adjusted under 35 U.S.C. 154(b) by 78 days.

(21) Appl. No.: 14/512,185

(22) Filed: Oct. 10, 2014

(65) Prior Publication Data

US 2016/0103083 A1    Apr. 14, 2016

(51) Int. Cl.
| | |
|---|---|
| *B61K 9/04* | (2006.01) |
| *B61K 9/06* | (2006.01) |
| *B61K 9/12* | (2006.01) |
| *G01N 25/72* | (2006.01) |
| *B61F 15/20* | (2006.01) |
| *G01J 5/08* | (2006.01) |
| *B61L 27/00* | (2006.01) |
| *G01J 5/00* | (2006.01) |

(52) U.S. Cl.
CPC .............. *G01N 25/72* (2013.01); *B61F 15/20* (2013.01); *B61K 9/04* (2013.01); *B61K 9/06* (2013.01); *B61K 9/12* (2013.01); *G01J 5/0022* (2013.01); *G01J 5/08* (2013.01); *B61L 27/0094* (2013.01); *G01J 2005/0081* (2013.01); *G06T 2207/10048* (2013.01)

(58) Field of Classification Search
CPC .............. B61K 9/04; B61K 9/06; B61K 9/12; G01J 2005/0077; G01J 2005/0071; G01J 5/08; B61L 27/0094; G06T 2207/10048
See application file for complete search history.

(56) References Cited

U.S. PATENT DOCUMENTS

| | | | | |
|---|---|---|---|---|
| 3,226,540 | A | * | 12/1965 | De Priest ................. B61K 9/06 246/169 D |
| 5,677,533 | A | * | 10/1997 | Yaktine ..................... B61K 9/04 246/169 A |
| 6,695,472 | B1 | | 2/2004 | Nayer |
| 6,872,945 | B2 | * | 3/2005 | Bartonek .............. G01J 5/0022 246/169 A |
| 7,698,962 | B2 | | 4/2010 | LeFebvre et al. |
| 7,752,015 | B2 | * | 7/2010 | Church .................... B61K 9/04 246/169 A |

(Continued)

FOREIGN PATENT DOCUMENTS

EP        1600351 B1     1/2007

*Primary Examiner* — Fadey Jabr
*Assistant Examiner* — Thomas Ingram
(74) *Attorney, Agent, or Firm* — Finnegan, Henderson, Farabow, Garrett & Dunner, LLP

(57) ABSTRACT

The present disclosure is directed to a method for detecting a condition associated with a wheel bearing on a train car. The method may include detecting a size and a location of the wheel bearing. The method may also include detecting a temperature associated with the wheel bearing based at least in part on the size and the location of the wheel bearing. The method may further include determining a wheel bearing condition based on the detected temperature.

17 Claims, 5 Drawing Sheets

(56) References Cited

U.S. PATENT DOCUMENTS

| | | | |
|---|---|---|---|
| 8,280,675 B2 * | 10/2012 | Church | B61K 9/04 702/130 |
| 8,439,315 B2 * | 5/2013 | Kilian | B61K 9/06 246/167 R |
| 2006/0180760 A1 * | 8/2006 | Lane | G01J 5/0022 250/339.05 |
| 2008/0028846 A1 * | 2/2008 | Heath | G01M 17/027 73/146 |
| 2008/0306705 A1 * | 12/2008 | Luo | B61K 9/04 702/134 |
| 2010/0100275 A1 * | 4/2010 | Mian | G01M 17/013 701/31.4 |
| 2013/0270396 A1 * | 10/2013 | Agostini | B61K 9/06 246/169 A |
| 2013/0270397 A1 | 10/2013 | Agostini | |
| 2013/0313372 A1 | 11/2013 | Gamache et al. | |
| 2014/0088801 A1 | 3/2014 | Bartonek | |
| 2014/0169398 A1 * | 6/2014 | Arndt | G01K 15/007 374/1 |

* cited by examiner

SYSTEM AND METHOD FOR DETECTING WHEEL BEARING CONDITION

TECHNICAL FIELD

The present disclosure relates generally to a detection system and method and, more particularly, a system and method for detecting a wheel bearing condition.

BACKGROUND

Monitoring systems for the railroad industry provide methods and apparatuses for automatic determination of the temperatures of components including wheels and wheel bearings on passing trains. Infrared (IR) radiation radiating from the wheel or wheel bearing of a train traveling along a train track is indicative of a temperature or temperature range of the wheel or wheel bearing. IR scanners and associated circuits for detecting an overheated wheel or wheel bearing are available commercially. Some systems utilize an IR detector located in close proximity to the railroad tracks. The IR detector determines the presence of radiated IR waves within a predefined range of wavelengths. The IR detector also produces an output signal indicative of the power or intensity of the sensed IR radiation within the predefined range.

One problem associated with these types of systems for detecting a temperature range or a temperature of a railroad train wheel or wheel bearing involves inaccuracies that may result under different conditions. For example, in situations where the range of detected IR waves is attenuated or filtered by external sources such as blowing snow, wind, rain, or other weather conditions, the result is an inaccurate detection of a hot wheel or hot bearing condition. Accurate detection of an overheated component such as a wheel or wheel bearing allows for corrective actions to be taken before the overheated component breaks down or fails.

One attempt to avoid the problem of inaccurate detection of wheel and bearing temperatures in a harsh environment is disclosed in U.S. Pat. No. 6,872,945 to Bartonek that issued on Mar. 29, 2005 (the '945 patent). The '945 patent discloses an apparatus that includes a sensor for sensing IR radiation radiating from a train wheel or bearing within two or more IR wavelength ranges, where each wavelength range does not substantially overlap with any other wavelength range. The sensor generates signals indicative of the sensed IR radiation in each of the wavelength ranges. A processor determines a temperature range or a temperature of the wheel or wheel bearing from the generated signals. The temperature detection system of the '945 patent may determine a temperature of a wheel or wheel bearing of a train traversing a railroad track. Furthermore, the temperature detection system of the '945 patent may not be susceptible to variations in the amplitude, intensity, or power of the detected IR radiation.

Although the temperature detection system of the '945 patent may be adequate for some applications, it may still be less than optimal. In particular, the temperature detection system of the '945 patent may detect a temperature associated with projected locations of the wheels or wheel bearings of the train. While this process may be accurate in some applications, it does not account for the precise location and size of the wheel or wheel bearings and, thus, may provide less accurate temperature readings of these components. The temperature detection system of the '945 patent may also not account for obstructions that restrict air flow to the wheels or wheel bearings of the train. The restriction of air flow can cause the wheels or wheel bearings to get warmer than normal, which can lead to false hot bearing detections that slow operations and reduce efficiencies of the train. Additionally, the temperature detection system of the '945 patent generally only considers the temperature of the wheels and/or wheel bearings of the train, without considering other wheel and wheel bearing conditions, such as, for example, movement of the wheels relative to the train track.

The system and method of the present disclosure solves one or more problems set forth above and/or other problems in the art.

SUMMARY

In one aspect, the present disclosure is directed to a method for detecting a condition associated with a wheel bearing on a train car. The method may include detecting a size and a location of the wheel bearing. The method may also include detecting a temperature associated with the wheel bearing based at least in part on the size and the location of the wheel bearing. The method may further include determining a wheel bearing condition based on the detected temperature.

In another aspect, the present disclosure is directed to a system for detecting a condition associated with a wheel bearing on a train car. The system may include at least one sensor configured to generate at least one thermal image, and a processor. The processor may be configured to detect a size and a location of the wheel bearing based on the at least one thermal image. The processor may also be configured to detect a temperature associated with the wheel bearing based on the at least one thermal image. The processor may further be configured to determine a wheel bearing condition based on the detected temperature.

In yet another aspect, the present disclosure is directed to a method for detecting a condition associated with a wheel bearing on a train car. The method may include receiving at least one thermal image from at least one sensor. The method may also include detecting a size and a location of the wheel bearing based on the at least one thermal image, and detecting a temperature associated with the wheel bearing based at least in part on the at least one thermal image and the size and the location of the wheel bearing. The method may further include determining whether an obstruction is located a predetermined distance from the wheel bearing. The method may further include determining a wheel bearing condition based on the detected temperature and the obstruction determination, and implementing a control action based on the determined wheel bearing condition.

DETAILED DESCRIPTION

Figure 1:
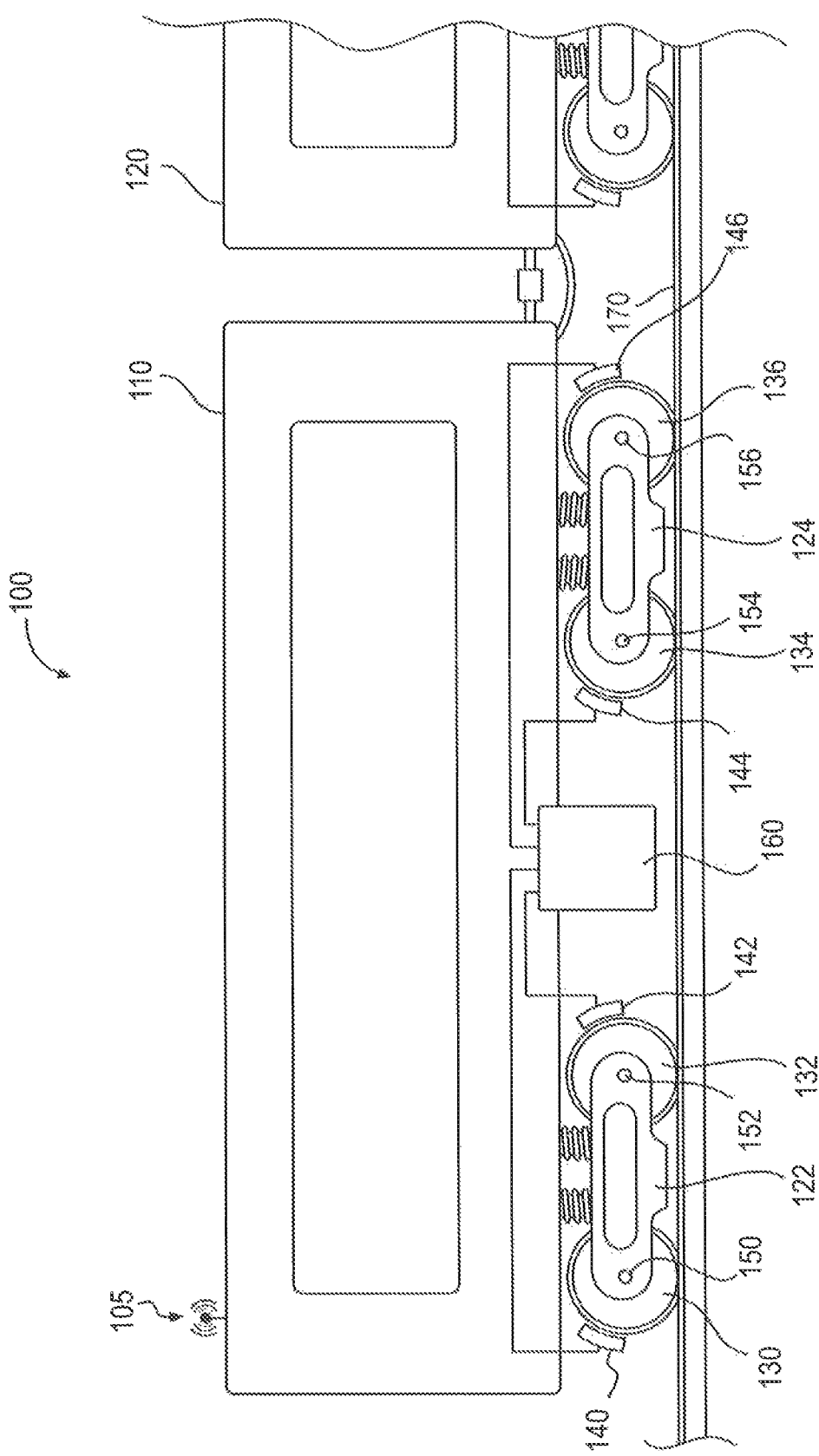
FIG. 1 is a diagrammatic illustration of an exemplary disclosed train.

FIG. 1 illustrates a portion of a train 100 including one or more cars 110, 120. Each car, such as shown for car 110, may include a plurality of trucks, such as trucks 122 and 124. A car may have as many as ten or more trucks, although more typically the number of trucks is two per car. Each truck 122, 124 may include two or more axles, with wheel bearings 150, 152 shown at one end of each of the axles on truck 122, and wheel bearings 154, 156 shown at one end of each of the axles on truck 124.

In addition, train 100 may include a pneumatic braking system, which may include a main air line from the locomotive (not shown), from which pressurized air is supplied to various brake valves, such as brake valve 160 shown in FIG. 1. Brake valve 160 may control the operation of one or more brake cylinders (not shown), which may control the actuation of one or more brakes 140, 142, 144, 146. Each brake 140, 142, 144, 146 may include friction material configured for contact against respective wheels 130, 132, 134, 136. One of ordinary skill in the art will recognize that other alternative brake systems may include disc brake systems or hydraulic fluid braking systems.

Figure 2:
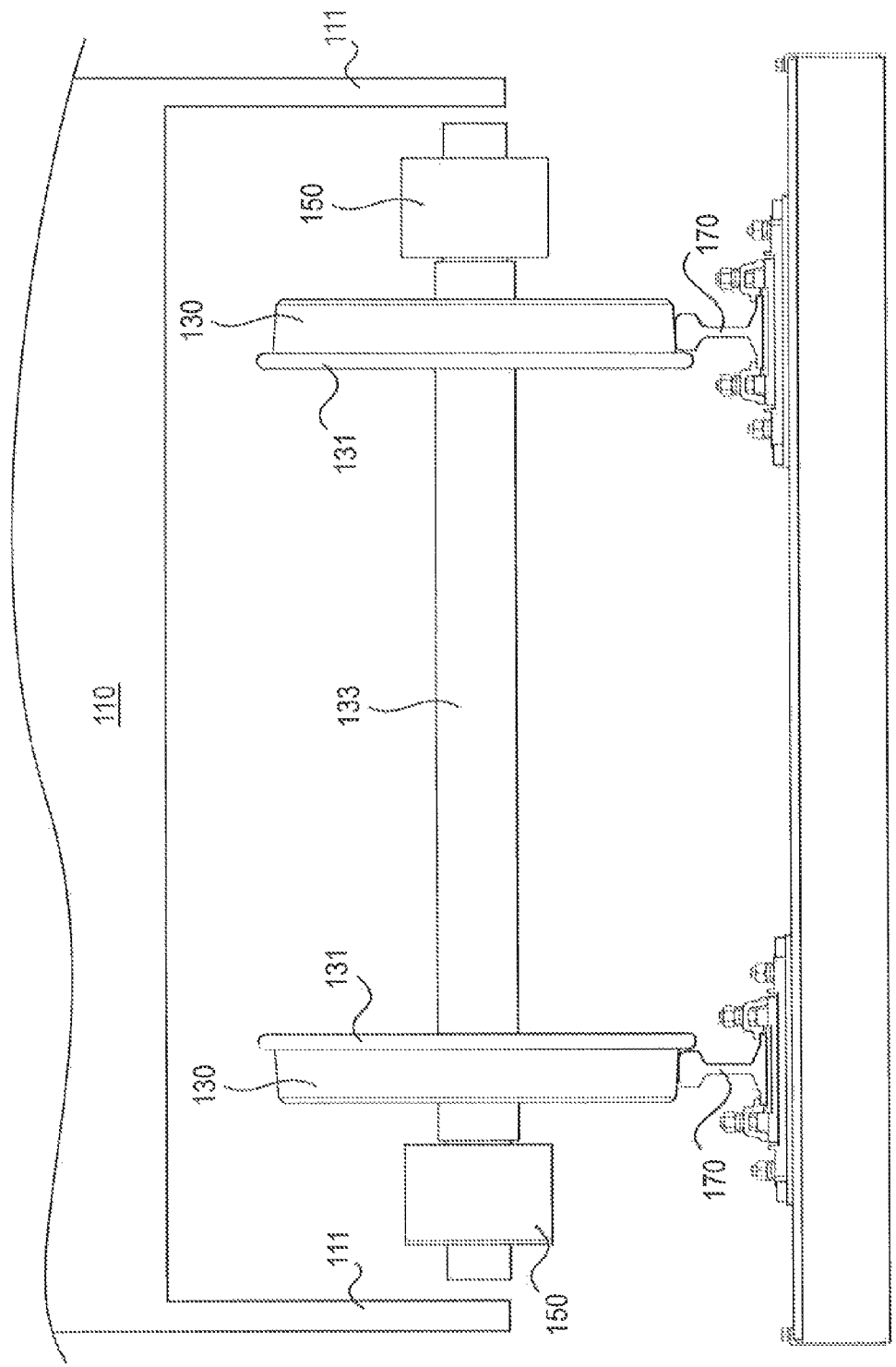
FIG. 2 is a diagrammatic illustration of an exemplary undercarriage portion of the train of FIG. 1.

In various implementations, wheels 130, 132, 134, 136 may be paired with matching wheels at the opposite ends of their respective axles. For example, as shown in FIG. 2, wheel 130 may be connected to a matching wheel 130 via an associated axle 133. Similarly, wheel bearing 150 may be paired with a matching wheel bearing 150 at the opposite end of axle 133. It is contemplated that, although only outer wheel bearings are shown in FIG. 2, one of ordinary skill in the art would recognize that inner wheel bearings may also be utilized, as desired.

As shown in FIG. 2, wheels 130 may include flanges 131 that are configured to guide wheels 130 along rails 170 of a train track. Although not shown in FIG. 2, matching wheels, matching wheel bearings, and flanges associated with each of the wheels may be associated with the other wheels 132, 134, 136 and wheel bearings 152, 154, 156 of train 100. Additionally, in some embodiments, train car 110 may include one or more portions 111 that extend downward to cover at least part of wheel bearings 150, such that the wheel bearings 150 may not be visible while standing at a location exterior to train 100.

During operation of the train, various components may wear out from continued use, and worn components may result in generation of excessive heat, which in turn may lead to failure of the components or potentially unsafe conditions. Therefore, various implementations of the present disclosure may monitor wheel temperatures and wheel bearing temperatures, as will be discussed in more detail below. In addition, various implementations of the present disclosure may also monitor one or more wheel conditions (e.g., movements of the wheels relative to the rails) and/or one or more wheel bearing conditions to prevent other potentially unsafe conditions (e.g., derailment of the train from the rails), as will be discussed in more detail below.

Figure 3:
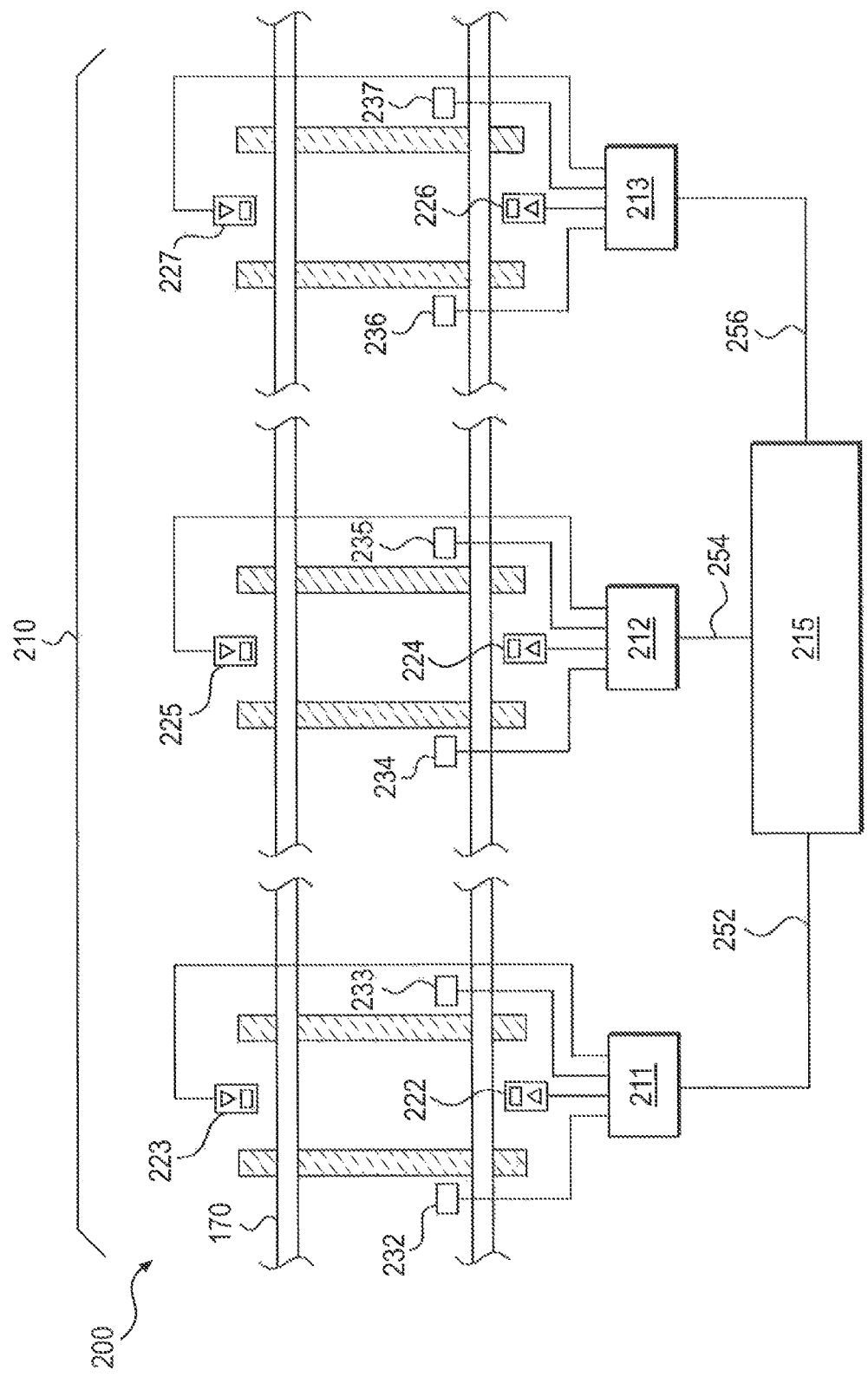
FIG. 3 is a schematic illustration of an exemplary disclosed detection system that may be used with the train of FIG. 1.

FIG. 3 illustrates an exemplary implementation of the disclosure directed to a detection system 200 for detecting one or more conditions of wheels 130, 132, 134, 136, and one or more conditions of wheel bearings 150, 152, 154, 156 on train cars 110, 120 (shown in FIG. 1) moving along rails 170 of the train track. Wayside detectors 211, 212, 213 may be positioned along rails 170 to automatically sense conditions of wheels 130, 132, 134, 136 or conditions of wheel bearings 150, 152, 154, 156 of a passing train. Signals output from detectors 211, 212, 213 may be processed to enable an alarm when the wheel or wheel bearing conditions are no longer safe for continued operation. Alternatively or additionally, the signals output from detectors 211, 212, 213 may assist in determining when to schedule preventative maintenance for avoidance of possible failures or unsafe conditions. For example, the alarm may be enabled when the wheel or wheel bearing temperatures become too great for continued safe operation, or when the sensed temperatures may be exhibiting a magnitude or trend in magnitudes that may assist in determining when to schedule preventative maintenance. The alarm may also be enabled when movements of one or more wheels 130, 132, 134, 136 relative to rails 170 are detected to be unsafe for continued operation, or are exhibiting a magnitude or trend in magnitudes that may assist in determining when to schedule preventative maintenance.

Detectors 211, 212, 213 in FIG. 3 may be positioned and configured to detect conditions of the wheels, wheel bearings, or other components of a passing train. Detectors 211, 212, and 213 may include temperature sensors 222-227, which are configured to convert sensed infrared (IR) radiation energy produced by a component such as a passing train wheel or wheel bearing to an electrical signal that is proportional to the amount of heat output by the wheel or wheel bearing relative to ambient temperature. Temperature sensors 222-227 may also detect photons emitted from an object being measured. Temperature sensors 222-227 may include, but are not limited to, IR non-imaging sensors, IR imaging sensors, photovoltaic sensors, piezoelectric sensors, pyroelectric sensors, and thermopile sensors. In one embodiment, temperature sensors 222-227 may include an IR imaging sensor, which may collect IR radiation at multiple points, which can form an array, and can provide data that may be used to create one or more thermal images.

Detectors 211, 212, 213 and temperature sensors 222-227 may be located in different positions relative to rails 170. Detectors 211, 212, 213, and temperature sensors 222-227 may be located in positions adjacent rails 170 and in between rails 170. They may also be located in housings configured to replace select ties provided to support rails 170 (sometimes referred to as "sleeper ties"). Other locations for temperature detectors 211, 212, 213, and temperature sensors 222-227, may include positions adjacent rails 170 and to the outside of rails 170, at angles looking up from ground level, at angles looking in a horizontal direction from an elevated position adjacent rails 170 and at approximately the height of wheel bearings 150, 152, 154, 156, and at angles looking down toward ground level from an elevated position adjacent rails 170. One of ordinary skill in the art will recognize that there are a variety of temperature sensing technologies suitable for use with various implementations of the disclosure.

As shown in FIG. 3, at least a first temperature sensor 222, and a second temperature sensor 223, may be disposed on opposite sides of rails 170 in order to be able to detect the temperatures of wheels or wheel bearings on both sides of a passing train car. Temperature sensors 224 and 225 associated with detector 212, may be positioned on opposite sides of rails 170 at the same location or at predetermined spacing, and at a predetermined spaced interval along rails 170 from detector 211. Optional additional pairs of temperature sensors associated with additional detectors, such as temperature sensors 226 and 227 associated with detector 213, may also be positioned on opposite sides of rails 170 at the same location or at predetermined spacing, and disposed at predetermined spaced intervals further along rails 170 in a direction of train travel along rails 170. In various exemplary implementations, the distance between each detector 211, 212, 213 may be any distance from several hundred yards, to approximately one half mile, to one mile or more.

The spaced pairs of temperature sensors may be included in a pre-designated detection area 210 along rails 170. Multiple detection areas similar to detection area 210 may be spaced along rails 170, with each detection area including two or more spaced pairs of temperature sensors. The detection areas may be located along stretches of train track over varying terrains. The pairs of temperature sensors 222 and 223, 224 and 225, and 226 and 227 placed along opposite sides of rails 170 may produce signals indicative of the temperatures for each wheel or wheel bearing on a per axle basis, and may provide those signals to associated detectors 211, 212, 213, respectively. Each detector 211, 212, 213 may also include associated position sensors 232 and 233, 234 and 235, and 236 and 237, respectively.

As a train car wheel passes each detector 211, 212, 213, the associated pairs of position sensors position sensors 232-237 may provide signals to the associated detectors 211, 212, 213. Each associated detector 211, 212, 213 may use the signals from position sensors 232-237 in defining a window when signals from associated temperature sensors 222-227 may be received and converted into temperatures of passing wheels 130, 132, 134, 136 or wheel bearings 150, 152, 154, 156. Each of detectors 211, 212, and 213 may be positioned at wayside stations along rails 170, and may be communicatively coupled with a processor 215 of detection system 200. Processor 215 may be located remotely from rail 170, in a dispatch office, on board the train, or in one or more wayside stations. Signals 252, 254, 256 may be communicated from detectors 211, 212, 213, respectively, to processor 215. One of ordinary skill in the art will recognize that signals 252, 254, and 256 may be communicated to processor 215 through a wireless connection, over an Ethernet connection, over a network, or through other means. Alternatively, each detector 211, 212, 213 may include an autonomous processor configured to perform various functions on the data received from temperature sensors 222-227 and from position sensors 232-237. It is contemplated that, in some embodiments, position sensors 232-237 may be omitted, and processor 215 and temperature sensors 222-227 may instead perform its functions.

Processor 215 may also be configured to only activate temperature sensors 222-227 of detectors 211, 212, and 213 when associated position sensors 232-237 indicate the presence of a wheel within the window between each pair of wheel position sensors. One of ordinary skill in the art will recognize that various implementations may include position sensors 232-237 comprising physical proximity transducers positioned adjacent train track 170, as shown in FIG. 3. In alternative implementations, the position of a wheel on a train car may be determined by other wheel position locators including devices that analyze a global positioning system (GPS) signal associated with a position of the train car. These wheel position locators may be located on the train 100, alongside the track 170, in wayside station houses, or in other remote locations. A GPS receiver 105 (shown in FIG. 1) may be located on a train car 110, 120 to provide wheel position location capabilities, identify where the train car is within detection area 210 at any time relative to the detectors, etc.

One of ordinary skill in the art will recognize that, although processor 215 is illustrated as a single unit, the functionality provided by processor 215 could be provided instead by one or more processors. The one or more processors may be part of a server, client, network infrastructure, mobile computing platform, or a stationary computing platform, one or more of which may be contained in a dispatch office, on the train, in a single wayside housing, multiple wayside housings, or at remote locations communicatively coupled over wired or wireless networks. Additionally, it is contemplated that temperature sensors 222-227 and position sensors 232-237 may have one or more associated processors to perform, for example, digitalization of signals and/or filtering the signals.

Detectors 211, 212, 213 capable of providing data indicative of the temperature of wheels 130, 132, 134, 136 and wheel bearings 150, 152, 154, 156 on a passing train 100 may include infrared (IR) sensors that react to IR radiation emitted by wheels 130, 132, 134, 136 and wheel bearings 150, 152, 154, 156 during operation of train 100 as a result of friction, transfers of vibrational energy, or other conditions that result in the generation of thermal energy. The IR detectors may receive IR radiation emitted from wheels 130, 132, 134, 136 or wheel bearings 150, 152, 154, 156 as a train passes the location of the IR detectors, and the IR radiation may be focused through one or more lenses, reflected by one or more reflective optics, or otherwise processed before reaching the IR detectors.

Various implementations of the present disclosure may provide data indicative of one or more wheel conditions and/or wheel bearing conditions of wheels 130, 132, 134, 136 and wheel bearings 150, 152, 154, 156 on a passing train 100 based on signals received from temperature sensors 222-227 and from position sensors 232-237. For example, processor 215 may be configured to receive signals 252, 254, and 256 from detectors 211, 212, 213, which may include one or more thermal images based on the signals received from temperature sensors 222-227 and from position sensors 232-237. Using the thermal images, processor 215 may be configured to determine positions of wheels 130, 132, 134, 136, wheel bearings 150, 152, 154, 156, and/or rail 170. Processor 215 may also be configured to use one or more predetermined spatial filtering algorithms to identify the size and locations of each of these components. In addition, processor 215 may be configured to detect a presence of any obstructions causing restriction in air flow to wheels 130, 132, 134, 136 and wheel bearings 150, 152, 154, 156. Based on these detections, processor 215 may determine various wheel conditions and/or wheel bearing conditions, and determine whether to implement a control action based on the detected wheel conditions and/or wheel bearing conditions.

Figure 4:
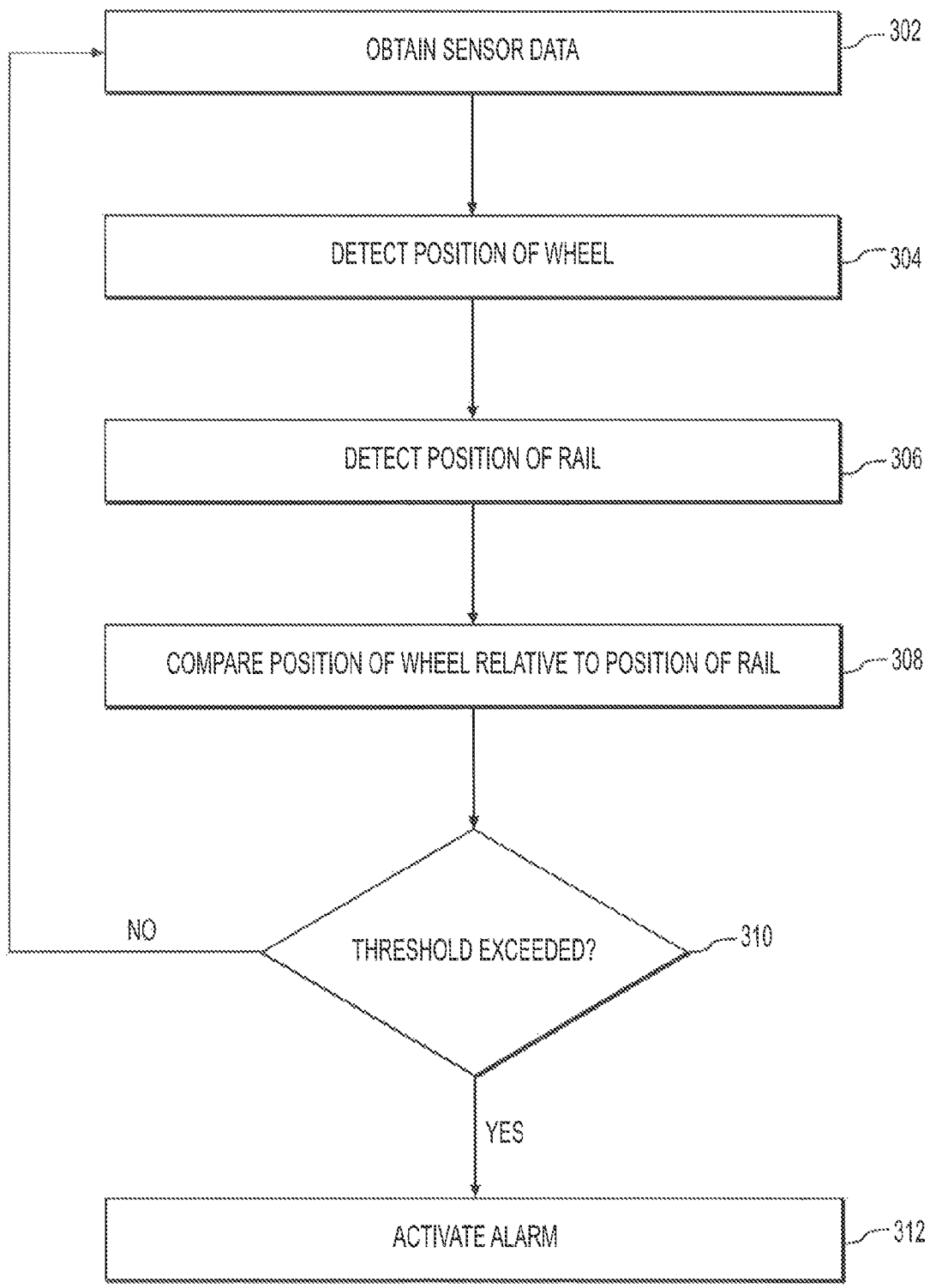
FIG. 4 is a flowchart depicting an exemplary disclosed method that may be performed by the system of FIG. 2.
Figure 5:
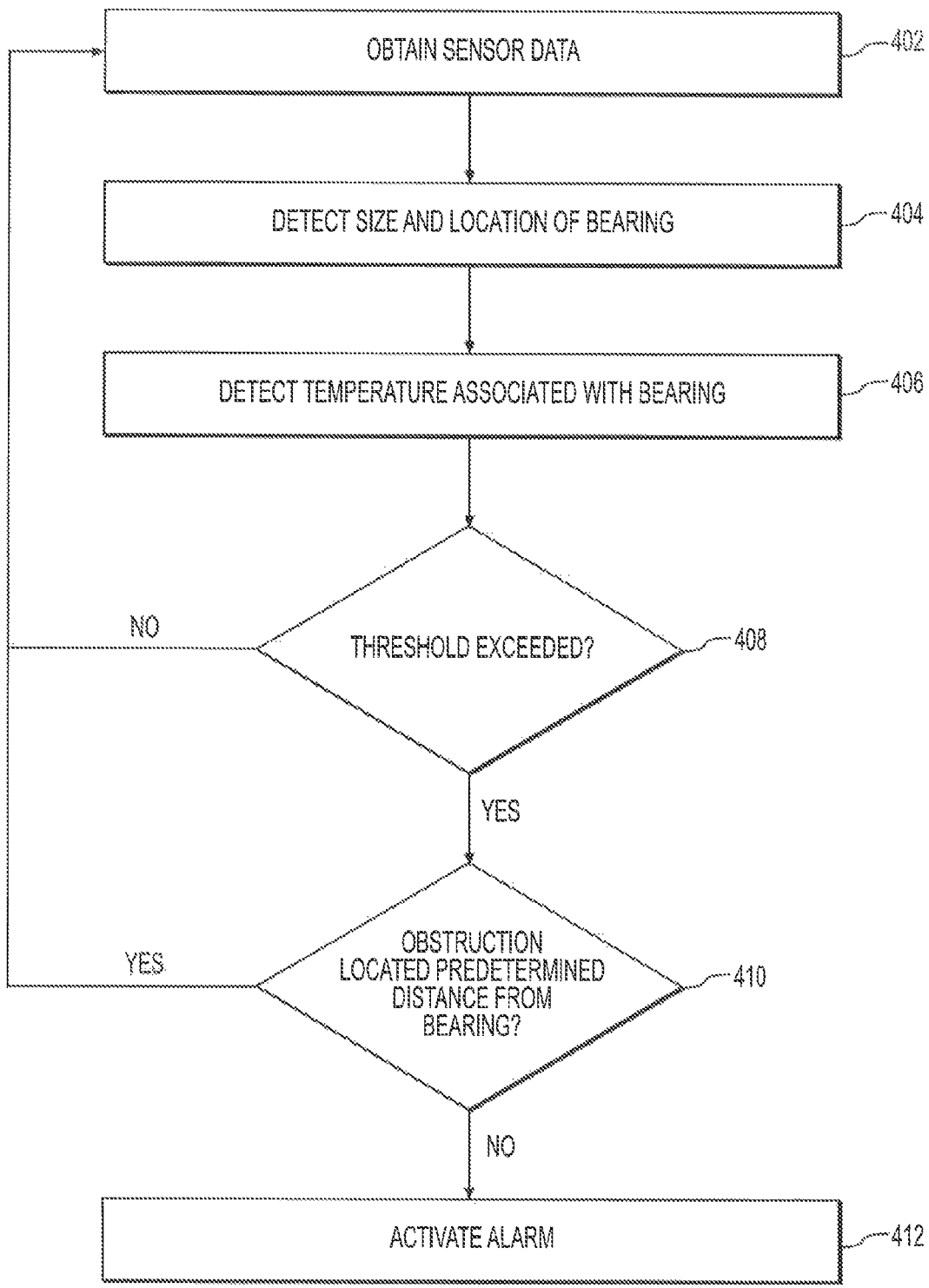
FIG. 5 is a flowchart depicting another exemplary disclosed method that may be performed by the system of FIG. 2.

FIGS. 4 and 5 are flowcharts depicting exemplary disclosed methods that may be performed by the system of FIG. 3. FIGS. 4 and 5 will be discussed in more detail below to further illustrate the disclosed concepts.

INDUSTRIAL APPLICABILITY

The disclosed method and system may allow for more accurate detection of wheel and wheel bearing temperatures as well as detecting potentially unsafe conditions associated with the wheels and the wheel bearings on a train car. Specifically, the disclosed method and system may detect the exact size and location of the wheels and the wheel bearings of the train car to more accurately determine temperatures associated with these components. In addition, the disclosed method and system may determine whether the movements of a wheel relative to rails on which the wheel travels are safe for continued operation. The disclosed method and system may further detect the presence of obstructions that restrict air flow to the wheels or wheel bearings. The detection of one or more of these wheel conditions and wheel bearing conditions may be used to identify when certain control actions should be taken, such as stopping the train to perform maintenance, scheduling future maintenance, performing autonomous control, etc.

Aspects of the present disclosure provide the functionality of detecting potentially unsafe operating conditions by tracking critical components of the train car through the use of the temperature and position sensors. The temperature sensors may output one or more thermal images, which may indicate excessive heating of wheels or wheel bearings of the train car. Aspects of the present disclosure may use spatial filtering algorithms to identify positions, sizes, and locations of the wheels and wheel bearings, in order to more accurately determine temperatures associated with these components. In addition, the spatial filtering algorithms may also allow the system to identify any obstructions restricting air flow to the wheels and wheel bearings. The restricted air flow may cause the temperatures of the wheels and wheel bearings to be higher than normal. By identifying the presence of these obstructions, false hot wheel or hot wheel bearing detections can be prevented with the use of spatial filtering algorithms. Aspects of the present disclosure may also detect various movements of the wheels relative to the rails in which they travel on. In certain situations, a flange of the wheel may be grinding against the rails at an angle or straight against the rails. This grinding may cause excessive wearing of the wheels and/or the rails, which can ultimately lead to unsafe conditions if not properly diagnosed or corrected. Also, if the flange is oscillating rapidly in a direction traverse to the rails (commonly known as "wheel hunting"), this may cause derailment of the train if the wheels were to become misaligned with the rails. Therefore, by detecting such wheel or wheel bearing conditions, derailment and/or excessive wearing of the wheels, wheel bearings, or rails can be prevented.

When one or more of these wheel conditions or wheel bearing conditions are detected, a processor 215 may be configured to implement a control action. The control actions implemented by the processor 215 may include, but are not limited to, sending an alert, sounding an alarm, sending instructions to be followed manually by a train operator, performing autonomous control of the train, scheduling maintenance functions to be performed at a later time, etc. Various implementations of this disclosure provide a detection system that may allow for the automated detection of wheel and/or wheel bearing conditions on every train car on a train as the train is moving along a train track.

Referring to FIG. 4, in one exemplary implementation, at step 302, processor 215 may obtain sensor data via signals 252, 254, and 256 from detectors 211, 212, 213 and associated temperature sensors 222-227 and position sensors 232-237. Then, at step 304, processor 215 may use the sensor data to detect a position of a wheel 130 of train 100 within a designated detection area 210 as the train 100 passes through the detection area 210. For example, signals output from temperature sensors 222-227 may provide one or more thermal images of train 100. Processor 215 may then detect a position of wheel 130 based on the thermal images using one or more spatial filtering algorithms. In some embodiments, processor 215 may also detect a position of flange 131 associated with wheel 130 using the thermal images and spatial filtering algorithms.

At step 306, processor 215 may detect a position of a rail 170 within detection area 210 as train 100 passes through the detection area 210. Similar to wheel 130, processor 215 may also use the thermal images and the spatial filtering algorithms to detect the position of the rail 170. Rail 170 may be the rail on which wheel 130 is travelling at the moment train 100 passes through the detection area 210.

At step 308, processor 215 may compare the detected positions of wheel 130 and rail 170. For example, processor 215 may determine a distance between wheel 130 and rail 170. In some embodiments, the distance may be a distance between flange 131 and rail 170. Alternatively or additionally, processor 215 may compare the detected positions of wheel 130 and rail 170 over a predetermined period of time. For example, the detected positions of wheel 130 and rail 170 may be detected at a first location at detector 211 and then again at a second location at detector 212 after the predetermined period of time. Based on the detected positions of wheel 130 and rail 170 and the time that elapsed while train 100 traveled between detectors 211 and 212, processor 215 may determine a velocity and/or an acceleration of wheel 130 relative to rail 170. The velocity and/or acceleration of wheel 130 may indicate, for example, potentially dangerous oscillation of wheel 130 in a direction traverse to rails 170.

At step 310, data gathered and processed by processor 215 may be used to identify when certain control actions should be taken, such as stopping the train to perform maintenance, scheduling future maintenance, and performing autonomous control. In some embodiments, a threshold value may be associated with a number of factors used in determining whether the control actions should be taken. For example, the threshold value may include information based on the distance between wheel 130 and rail 170, a velocity of wheel 130 relative to rail 170, and/or an acceleration of wheel 130 relative to rail 170. The threshold value may be exceeded when the distance between wheel 130 and rail 170 is less than a predetermined distance, when the velocity of wheel 130 relative to rail 170 is higher than a predetermined velocity, and/or when the acceleration of wheel 130 relative to rail 170 is higher than a predetermined acceleration. At step 310, if the threshold value is exceeded, then processor 215 may generate one or more control actions (e.g., activate an alarm) at step 312. Otherwise, the process may return to step 302 to receive more sensor data.

Referring to FIG. 5, in another exemplary implementation, at step 402, processor 215 may obtain sensor data via signals 252, 254, and 256 from detectors 211, 212, 213 and associated temperature sensors 222-227 and position sensors 232-237. Then, at step 404, processor 215 may use the sensor data to detect a size and a location of a wheel bearing 150 within a designated detection area 210 as train 100 passes through the detection area 210. For example, signals output from temperature sensors 222-227 may provide one or more thermal images. Processor 215 may then detect the size and the location of a wheel bearing 150 based on the thermal images using one or more spatial filtering algorithms. In addition to detecting the size and the location of wheel bearing 150, it is contemplated that processor 215 may also detect the size and the location of a wheel 130 based on the thermal images using one or more spatial filtering algorithms.

At step 406, processor 215 may use the detected size and location of wheel bearing 150 to detect a temperature associated with wheel bearing 150. Specifically, using the thermal images and the spatial filtering algorithms, processor 215 may determine an exact size and location of wheel bearing 150 in the thermal images and extract thermal imaging data based on the size and location of wheel bearing 150. In some embodiments, processor 215 may extract thermal imaging data across an entire bearing cup (not shown) associated with wheel bearing 150. The bearing cup may cover, for example, one or more bearing assemblies of wheel bearing 150. As a result, this process may provide a more accurate temperature reading than other systems, which tend to predict a size and location of the wheel bearings rather than determine the size and location based on thermal images. In addition to a temperature associated with wheel bearing 150, it is contemplated that processor 215 may also detect a temperature associated with wheel 130 using the thermal images and the spatial filtering algorithms.

At step 408, processor 215 may determine whether the temperature of wheel bearing 150 exceeds a threshold value. For example, if the temperature of wheel bearing 150 is greater than a threshold temperature, then the process may proceed to step 410. Otherwise, the process may return to step 402 to receive more sensor data.

At step 410, processor 215 may determine whether an obstruction has caused the wheel bearing temperature to become abnormally warm. For example, one such obstruction may be a portion 111 (shown in FIG. 2) of train car 110 that covers at least part of wheel bearings 150, thereby restricting air flow to wheel bearings 150. Although the restricted air flow may cause the wheel bearing temperature to become abnormally warm, this does not necessarily mean that wheel bearing 150 is subject to a hot bearing condition. Therefore, if an obstruction is not located a predetermined distance from wheel bearing 150, then processor 215 may generate one or more control actions (e.g., activate an alarm) at step 412. Otherwise, the process may return to step 402 to receive more sensor data.

It will be apparent to those skilled in the art that various modifications and variations can be made to the disclosed detection system without departing from the scope of the disclosure. Other embodiments of the detection system will be apparent to those skilled in the art from consideration of the specification and practice of the detection system disclosed herein. It is intended that the specification and examples be considered as exemplary only, with a true scope of the disclosure being indicated by the following claims and their equivalents.

What is claimed is:

1. A method for detecting a condition associated with a wheel bearing on a train car, the method comprising:
   generating a thermal image with a sensor;
   determining with a processor a size and a location of the wheel bearing based on the thermal image;
   determining with the processor a temperature associated with the wheel bearing based at least in part on the size and the location of the wheel bearing and based on the thermal image;
   determining with the processor a wheel bearing condition based on the temperature; and
   selectively implementing with the processor a control action associated with the train car based on the wheel condition.

2. The method of claim 1, wherein determining the temperature associated with the wheel bearing includes extracting thermal imaging data based on the size and the location of the wheel bearing and using the thermal imaging data to determine the temperature associated with the wheel bearing.

3. The method of claim 1, further including spatially filtering the thermal image to determine the size and the location of the wheel bearing.

4. The method of claim 1, wherein implementing the control includes implementing the control action only when the temperature associated with the wheel bearing is greater than a threshold temperature.

5. The method of claim 1, further including determining whether an obstruction is located a predetermined distance from the wheel bearing.

6. The method of claim 5, wherein implementing the control further includes implementing the control action only when no obstruction is located the predetermined distance from the wheel bearing.

7. The method of claim 5, inhibiting implementation of the control action when the obstruction is located the predetermined distance from the wheel bearing.

8. The method of claim 5, wherein the obstruction includes a portion of the train car that covers at least part of the wheel bearing.

9. A system for detecting a condition associated with a wheel bearing on a train car, the system comprising:
   at least one sensor configured to generate at least one thermal image; and
   a processor configured to:
      determine a size and a location of the wheel bearing based on the at least one thermal image;
      determine a temperature associated with the wheel bearing based at least in part on the at least one thermal image and the size and the location of the wheel bearing;
      determine a wheel bearing condition based on the detected temperature; and
      implement a control action associated with the train car based on the wheel bearing condition.

10. The system of claim 9, wherein the processor is further configured to extract thermal imaging data based on the size and the location of the wheel bearing, and use the thermal imaging data to determine the temperature associated with the wheel bearing.

11. The system of claim 10, wherein the processor is further configured to spatially filter the at least one thermal image to determine the size and the location of the wheel bearing.

12. The system of claim 9, wherein the processor is further configured to implement the control action only when the detected temperature is greater than a threshold temperature.

13. The system of claim 9, wherein the processor is further configured to determine whether an obstruction is located a predetermined distance from the wheel bearing.

14. The system of claim 13, wherein the processor is further configured to implement the control action only when no obstruction is located the predetermined distance from the wheel bearing.

15. The system of claim 13, wherein the processor is further configured to inhibit implementation of the control action when the obstruction is located the predetermined distance from the wheel bearing.

16. The system of claim 13, wherein the obstruction includes a portion of the train car that covers at least part of the wheel bearing.

17. A method for detecting a condition associated with a wheel bearing on a train car, the method comprising:
   receiving at least one thermal image from at least one sensor;
   determining a size and a location of the wheel bearing based on the at least one thermal image;
   determining a temperature associated with the wheel bearing based at least in part on the at least one thermal image and the size and the location of the wheel bearing;
   determining whether an obstruction is located a predetermined distance from the wheel bearing;

determining a wheel bearing condition based on the detected temperature and a location of the obstruction; and implementing a control action associated with the train car based on the wheel bearing condition.

\* \* \* \* \*

UNITED STATES PATENT AND TRADEMARK OFFICE
CERTIFICATE OF CORRECTION

PATENT NO. : 9,518,947 B2  
APPLICATION NO. : 14/512185  
DATED : December 13, 2016  
INVENTOR(S) : Bartonek et al.

Page 1 of 1

It is certified that error appears in the above-identified patent and that said Letters Patent is hereby corrected as shown below:

On the Title Page

Column 1, Item (72) (Inventors), Line 4, delete "MD (US)" and insert -- MO (US) --.

Signed and Sealed this  
Fourth Day of April, 2017

Michelle K. Lee  
*Director of the United States Patent and Trademark Office*